(12) United States Patent
Skell

(10) Patent No.: US 10,183,131 B1
(45) Date of Patent: Jan. 22, 2019

(54) EXTRACTING THERAPEUTIC SUBSTANCES FROM BOTANICAL MATTER

(71) Applicant: Jeffrey M. Skell, Westborough, MA (US)

(72) Inventor: Jeffrey M. Skell, Westborough, MA (US)

( * ) Notice: Subject to any disclaimer, the term of this patent is extended or adjusted under 35 U.S.C. 154(b) by 73 days.

(21) Appl. No.: 14/807,112

(22) Filed: Jul. 23, 2015

Related U.S. Application Data

(60) Provisional application No. 62/029,036, filed on Jul. 25, 2014.

(51) Int. Cl.
*A61M 11/04* (2006.01)
*A61M 16/06* (2006.01)

(52) U.S. Cl.
CPC .......... *A61M 11/041* (2013.01); *A61M 16/06* (2013.01); *A61M 2205/3331* (2013.01)

(58) Field of Classification Search
CPC ........................... A61M 11/041; A61M 16/06
See application file for complete search history.

(56) References Cited

U.S. PATENT DOCUMENTS

| | | | | | |
|---|---|---|---|---|---|
| 3,949,743 | A | * | 4/1976 | Shanbrom | A61H 33/12 128/200.14 |
| 4,735,217 | A | * | 4/1988 | Gerth | A24F 47/008 128/203.17 |
| 4,807,646 | A | * | 2/1989 | Sahar | A24F 13/16 131/175 |
| 4,945,928 | A | * | 8/1990 | Rose | A24B 15/165 131/270 |
| 6,270,708 | B1 | * | 8/2001 | Gurol | B02C 13/18 264/117 |
| 6,772,756 | B2 | * | 8/2004 | Shayan | A61M 11/041 128/202.21 |
| 2011/0059205 | A1 | * | 3/2011 | Gaysinsky | A23G 4/068 426/66 |
| 2014/0287121 | A1 | * | 9/2014 | Gaysinsky | A23G 4/068 426/538 |

\* cited by examiner

*Primary Examiner* — Regina M Yoo
(74) *Attorney, Agent, or Firm* — Anderson Gorecki LLP

(57) ABSTRACT

An extraction system uses a sample of botanical matter which has been rendered into particles of a predetermined range of sizes and compressed into a non-flowable form. The sample is loaded into an extraction chamber which may be sealed. A conductive or convective heat source is used to heat the loaded sample to a temperature which causes at least one substance within the sample to vaporize. A conduit can be used to transfer vapor resulting from vaporization of the substance to a collection chamber and mask. Pressure may be adjusted within the system to facilitate vaporization and vapor transport.

15 Claims, 8 Drawing Sheets

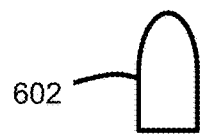
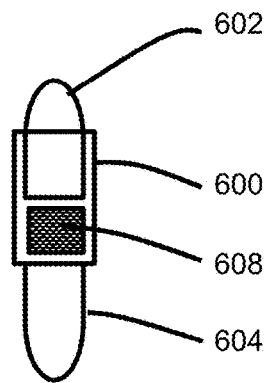
Figure 6A    Figure 6B
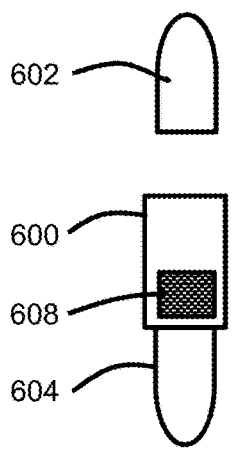
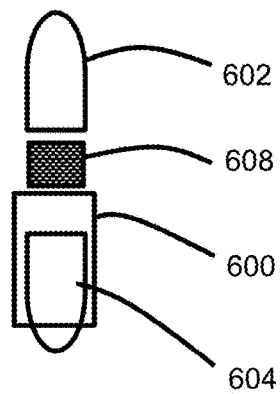
Figure 6C    Figure 6D

EXTRACTING THERAPEUTIC SUBSTANCES FROM BOTANICAL MATTER

CROSS-REFERENCE TO RELATED APPLICATIONS

This application claims benefit from U.S. Provisional Patent Application No. 62/029,036, filed Jul. 25, 2014, entitled SYSTEM AND METHOD FOR ANEROBIC VAPORIZATION, the contents of which are incorporated herein by reference.

BACKGROUND

The subject matter of this disclosure relates generally to processing of botanical matter to extract and administer therapeutic substances found therein. A variety of substances used in medicine are found in botanical matter. For example, willow trees produce salicylic acid which is the active metabolite of aspirin. Ginger has long been known for counteracting nausea. *Cannabis*, which has more recently become recognized for its medicinal properties, contains substances which have therapeutic value for patients with chronic pain, multiple sclerosis, epilepsy and HIV/Aids. Unlike some other botanical matter with medicinal use, *cannabis* is typically combusted and administered via inhalation of smoke. This is problematic because combustion may produce unwanted and unhealthy by-products. It is known to extract substances of interest from botanical matter to produce a liquid solution. The liquid solution can then be vaporized by a delivery system. The resulting vapor, which typically does not contain all of the unwanted and unhealthy by-products of combustion, is inhaled by the user. "E-cigarettes" are an example of a system based on vaporization of substances in a liquid solution.

SUMMARY

All examples and features mentioned below can be combined in any technically possible way. Moreover, potential advantages described herein are not necessarily associated with all implementations, and none of the advantages are required to be realized in order to practice the inventive concepts disclosed herein.

In accordance with one aspect a system comprises: a sample of botanical matter which has been rendered into particles of a predetermined range of sizes and compressed into a non-flowable form; an extraction chamber into which the sample is loaded; a heat source which applies heat to the loaded sample, the heat causing at least one substance within the sample to vaporize; and a conduit via which vapor resulting from vaporization of the substance is captured from the extraction chamber and delivered to at least one destination. In some implementations the destination comprises a vapor collection chamber. In some implementations the system comprises a device which changes pressure in the vapor collection chamber. In some implementations the vapor collection chamber comprises a syringe. In some implementations the destination comprises a device which facilitates inhalation of the vapor. In some implementations the device which facilitates inhalation of the vapor comprises a facemask. In some implementations the destination comprises a vapor collection chamber and vapor delivery device, and in which a valve interconnects the extraction chamber with the vapor collection chamber in a first state, and in which the valve interconnects the vapor collection chamber with the vapor delivery device in a second state. In some implementations the system comprises a cap which seals the extraction chamber. In some implementations the sample occupies substantially all of the extraction chamber. In some implementations the heat source comprises a conductive heat source. In some implementations the heat source comprises a convective heat source. In some implementations the sample is heated to at least a boiling point of the substance but not to a decomposition temperature of the sample. In some implementations the sample is heated to at least a combustion temperature of the sample. In some implementations the extraction chamber comprises a blunt end needle. In some implementations the sample is rendered into particles of a predetermined range of sizes in a wet milling process in which feedstock has a moisture content of at least 20% by weight. In some implementations the system comprises a ram extruder which renders the sample. In some implementations the system comprises a ram extruder which renders the sample in a continuous extrusion process. In some implementations the system comprises a controlled atmosphere chamber in which the rendered feedstock is dried. In some implementations the system comprises a press which pelletizes the dried rendered feedstock. In some implementations the system comprises an extruder which pelletizes the dried rendered feedstock.

Using compressed milled feedstock, e.g., pellets, may provide some advantages in some implementations. For example, compressed milled feedstock helps to reduce the amount of oxygen present in the extraction chamber. Further, therapeutic substances are more evenly distributed in milled feedstock, and milled feedstock can be more readily tested and blended prior to being compressed in order to provide a product having known characteristics which may provide more predictable results. Further, desirable substances that might be lost due to other processing techniques may be retained. Pelletized feedstock may also facilitate packaging, storage and delivery.

Vaporization may have some advantages in some implementations. For example, Vaporization may help to provide more efficient extraction and delivery of substances of interest in comparison with combustion. Moreover, vaporization may avoid production of undesirable and unhealthy smoke from combustion.

Aspects of the extraction and delivery system may have some advantages in some implementations. For example, a sealed extraction chamber may help to exclude oxygen and thereby facilitate an anaerobic extraction process. Vapor purity may be improved by excluding oxygen from the extraction chamber while the feedstock is heated. Further, an anaerobic process is less likely to inadvertently create combustion. Application of a vacuum during vaporization may also help by reducing the boiling point temperature of certain volatile substances of interest and to avoid inadvertent combustion when their boiling point is close to the combustion temperature of the feedstock. A closed system also facilitates the production of a more pure vapor concentrate, e.g., by avoiding or reducing mixing extracted vapor with air.

BRIEF DESCRIPTION OF THE DRAWINGS

FIGS. 6A, 6B, 6C and 6D illustrate a pellet press.

DETAILED DESCRIPTION

Exemplary implementations of the invention will now be described with regard to the attached figures. It should be understood that although certain representative structures, arrangements and materials will be introduced in the description, such structures, arrangements and materials are provided by way of example only, and not as limitations. A wide variety of combinations, replacements or modifications are both possible and within the scope of the concepts.

Figure 1:
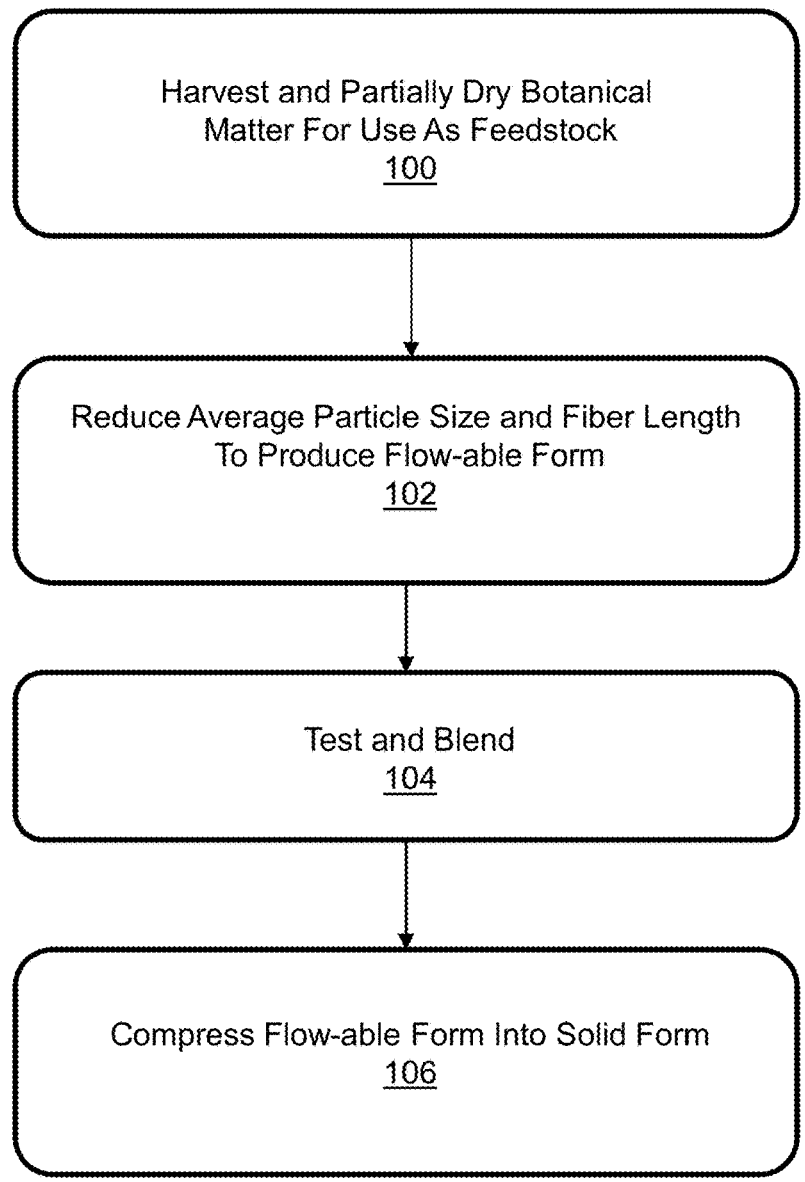
FIG. 1 illustrates a process for preparing botanical matter for vaporization.

FIG. 1 illustrates a process for preparing botanical matter for an extraction process, e.g., vaporization. Feedstock is produced from harvested botanical matter in step 100. Although *cannabis* is described herein as the exemplary botanical matter being processed, the concepts described herein are not limited to *cannabis*. The botanical matter used to provide feedstock may include any of a wide range of different plants and combinations of different plants. Moreover, entire plants or selected parts of plants may be processed. The moisture content of freshly harvested green plant material may support undesirable microbiological growth. However, rapid drying such as with heat or vacuum may inhibit desirable maturation of the botanical matter. Moreover, freshly harvested botanical matter may include desirable "inactive" phytochemicals that could be lost as a result of drying or overly rapid drying. These phytochemicals may contribute to characteristics such as taste, aroma, and possibly biodistribution and receptor binding of one or more active components. Consequently, partial drying, curing, protection from microbiological growth, and protection from loss of desirable volatile components are implementation details which may be determined based on the characteristics of the botanical matter being processed and desired results. For example, in order to mitigate loss of inactive phytochemicals a partial drying process may include implementation of a drying schedule characterized by periods during which moisture content is reduced at a controlled rate alternating with periods during which moisture content is held stable. In some implementations the harvested botanical matter is conventionally air dried to 8%-15% moisture by weight. Alternatively, the plant matter may be partially dried, e.g., to reduce the moisture content to a range of 33%-50% moisture by weight, and then stored for some time in a sealed container, e.g., a couple days, to effect a curing process. Subsequent to the curing step the partially dried plant matter may be further dried to reduce the final moisture content below that supporting microbiological growth.

Step 102 is to process the feedstock into a flow-able form. This may be accomplished by rendering the feedstock into a smaller target range of particle size and fiber length, e.g. via a milling process. The harvested material may include particles and fibers in a wide range of sizes and lengths. Average particle size and average fiber length can be reduced via the milling process, e.g., to 2.5-mm. Moreover, the distribution of particle sizes and fiber lengths can be controlled to within a predetermined range, e.g., to 0.5-10 mm. A wide variety of milling and other techniques might be employed. For example, and without limitation, milling may include the application shearing force, compression force, or both.

Figure 2A:
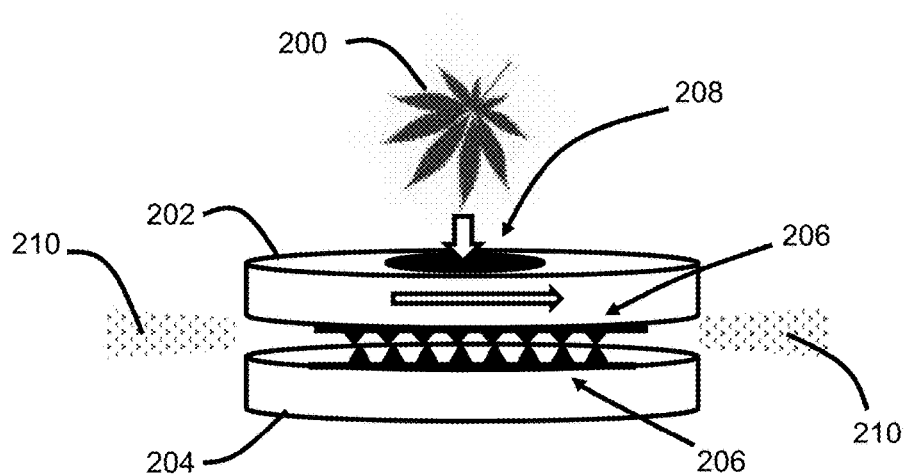
FIG. 2A illustrates a burr grinder.

As illustrated in FIG. 2A, a burr grinder applies shearing force by passing feedstock 200 between two surfaces which are in motion relative to each other. The surfaces may include disks 202, 204, which may be counter-rotating disks or one of which may be rotating while the other remains stationary. The paired disks may have burrs 206 formed on corresponding parallel faces, although other configurations are possible. Shearing force is applied as burrs on the corresponding surfaces come into close proximity with feedstock positioned there between. Feedstock 200 may be introduced to the grinder via a central opening 208 in disk 202, e.g., gravity fed. Milled feedstock 210 is expelled from the grinder proximate to the outer edges of the disks 202, 204.

Figure 2B:
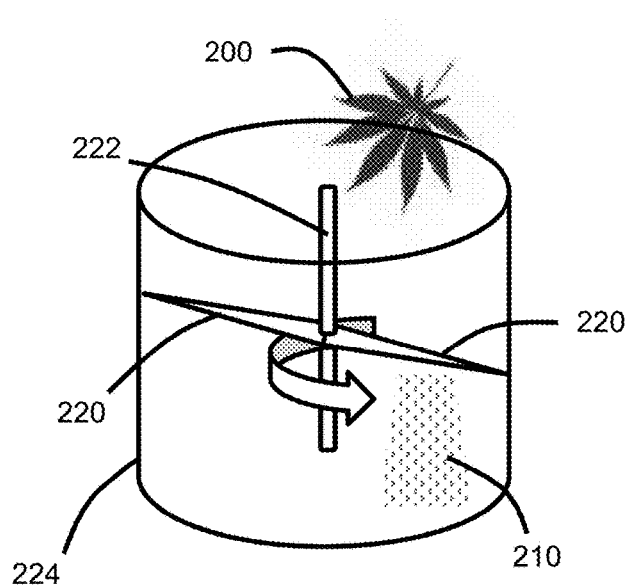
FIG. 2B illustrates a blade grinder.

As illustrated in FIG. 2B, a blade grinder applies shearing force with high speed blades 220. The blades may be attached to a rotating shaft 222 which is driven by an electric motor. Distal ends of the blades may be proximate to an inner surface of a milling chamber 224 having a circular cross-section. Feedstock 200 is fed into the chamber, e.g., by gravity, and the rotating blades 220 apply a shearing force to the feedstock at the point of contact between the blade and the feedstock. Milled feedstock 210 is expelled at a second distal end of the milling chamber.

Figure 3A:
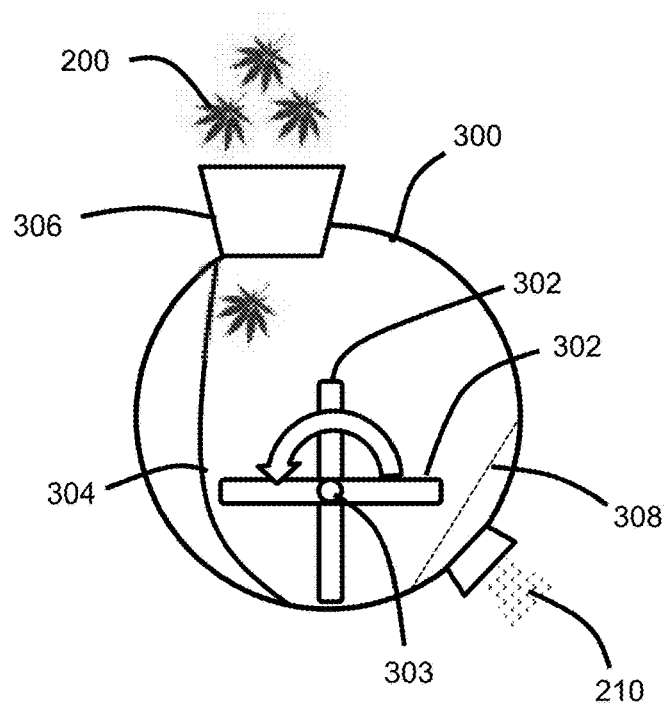
FIG. 3A illustrates a hammer mill.

As illustrated in FIG. 3A, compression force may be applied with a hammer mill, for example and without limitation. The hammer mill includes a milling chamber 300 and rotating hammers 302 positioned therein. The hammers are connected to a drive shaft 303 which may be driven by an electric motor. A contoured inner wall surface 304 within the chamber 300 has limited and possibly adjustable clearance relative to distal ends of the rotating hammers 302 for a portion of the range of rotation. Feedstock 200 is fed into the chamber 300 via a hopper 306 and provided to a location proximate to the contoured surface 304. Compression force is applied as the feedstock is positioned in the area of limited clearance between the rotating hammers 302 and the contoured surface 304. Rotation of the hammers also helps to move the processed feedstock to an ejection area. A screen 308 may be used to allow expulsion of milled feedstock 210 while retaining feedstock that has not been sufficiently rendered to pass through the screen. Rotation of the hammers also helps to cause the retained feedstock to be repeatedly passed between the hammers and the contoured surface until it has been sufficiently rendered so that it can traverse the screen.

Figure 3B:
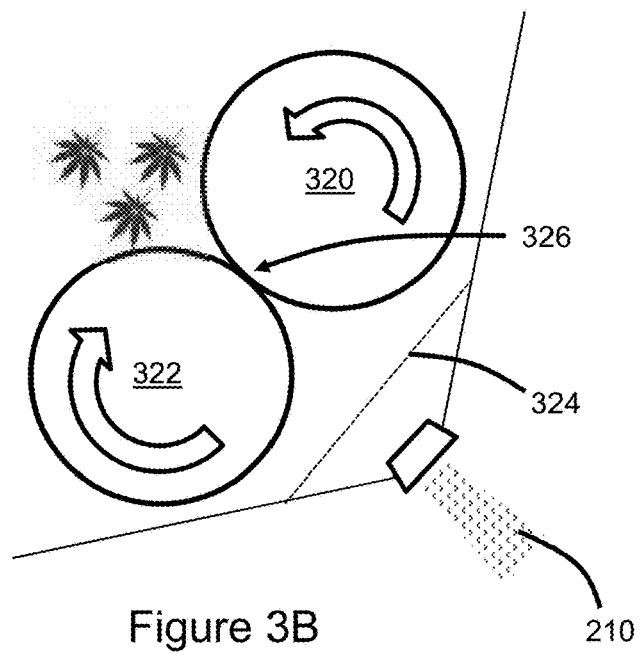
FIG. 3B illustrates a roller mill.

As illustrated in FIG. 3B compression force may be applied with a roller mill, for example and without limitation. The roller mill may include two counter-rotating drums 320, 322 driven by an electric motor. Compression force is applied at a point 326 of limited clearance or contact between the drums 320, 322. Milled feedstock 210 may be separated from feedstock that has not yet been sufficiently milled with a screen 324. Feedstock which cannot pass through the screen may be reprocessed.

The milling techniques described above require dried feedstock with moisture content below about 20% by weight, and typically between 8%-15%, where the plant material undergoes brittle fracture. Milling feed stock at a higher water content can be accomplished via a process that doesn't rely on brittle fracture to accomplish particle size reduction. Two examples of suitable processes are described below.

Figure 4:
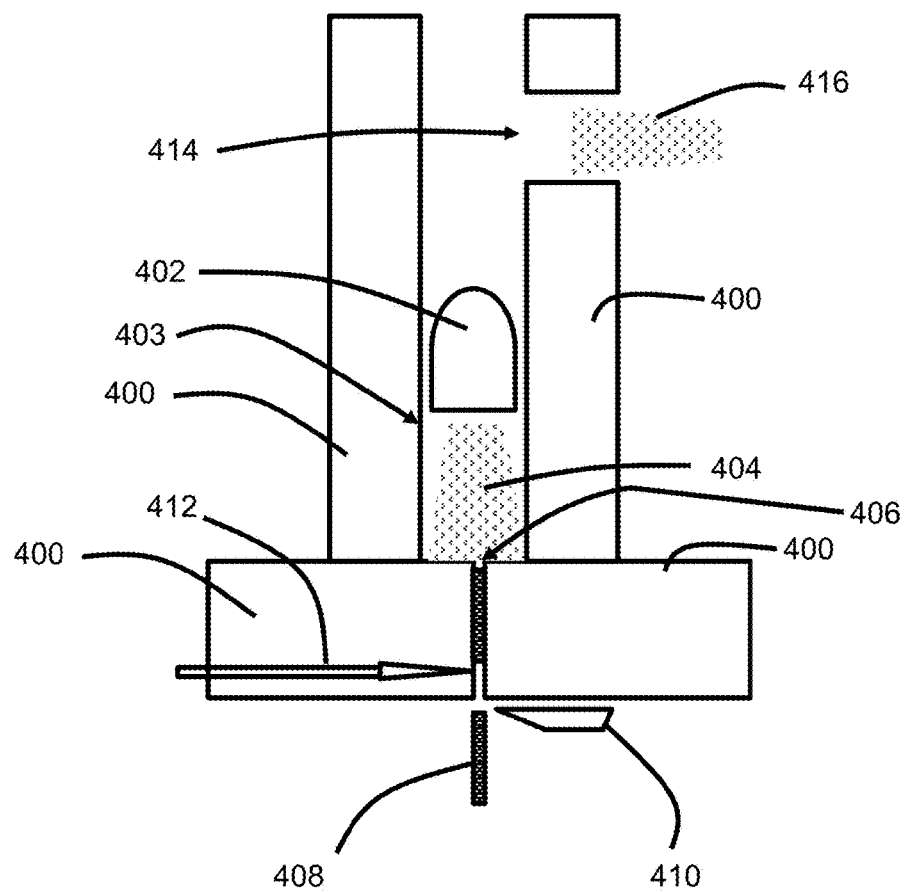
FIG. 4 illustrates a ram extruder.

FIG. 4 illustrates an exemplary ram extruder. The ram extruder includes a movable piston 402 and walls 400 which form a compression chamber 403 in which the piston moves. The piston 402, which has limited clearance relative to the chamber walls, is used to apply force to a charge of loose milled feedstock 404 that has been loaded into the compression chamber. Force may be applied to the piston mechanically, e.g., a lever arm, or otherwise, e.g., pneumatically. A discharge port 406 of predetermined diameter is formed in a first distal end of the compression chamber. Feedstock is extruded via the discharge port when sufficient pressure has been applied to feedstock 404 in the chamber by the piston 402. A cutter 410 can be used to cut the extruded feedstock at a specified length, thereby providing a pellet 408. The discharge port can be fitted with an adjustable needle 412 to enable application and adjustment of a desired amount of back-pressure to control and adjust shear force and feed rate, e.g., adjusting the port 406 from fully open to fully closed and any state there between. Once the down stroke is complete the piston 402 is pulled away from the port 406 in an upstroke. For example, the piston may be moved beyond an intake port 414 so that the compression chamber can be reloaded with another charge of milled feedstock 416. Force is then applied to the piston and the down stroke is repeated. A ram extruder is one example of a milling apparatus for milling feedstock with moisture content above 8%-15% and even above 20% by weight without reliance on brittle fracture.

Figure 5:
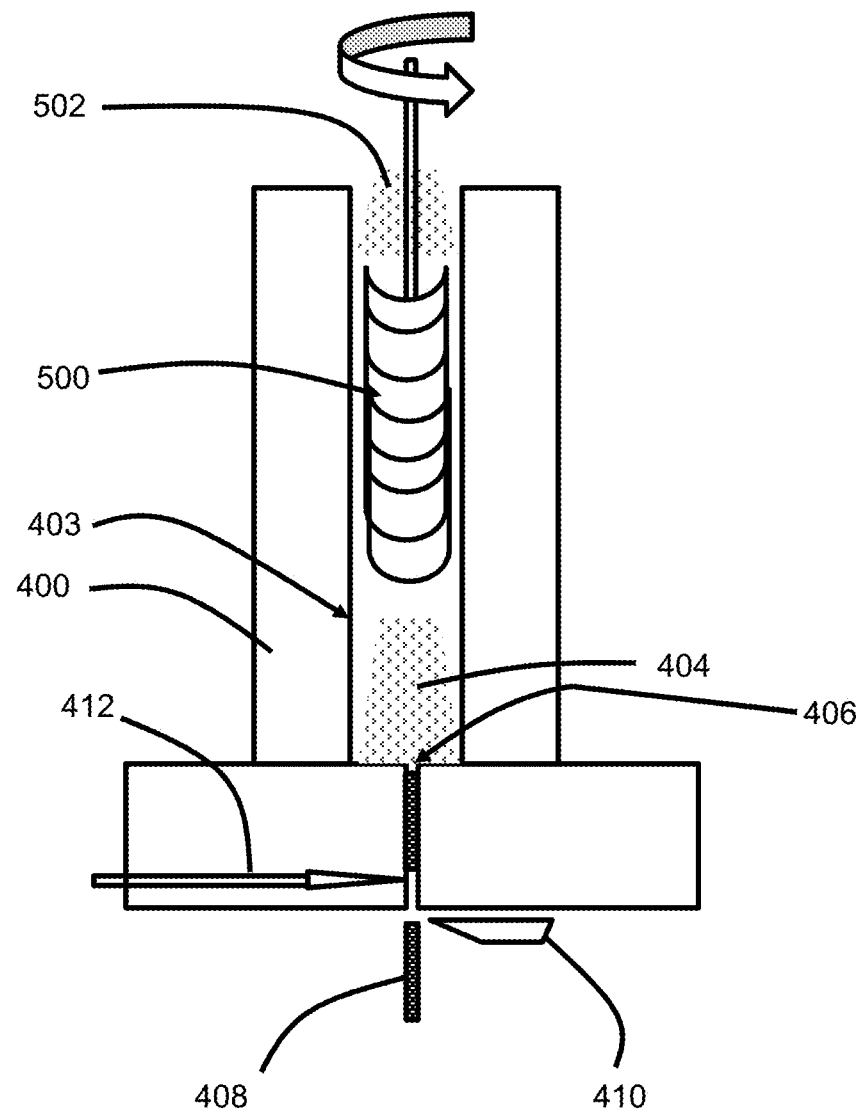
FIG. 5 illustrates a continuous feed extruder.

As shown in FIG. 5, a continuous extrusion process can be achieved by using a rotating screw extruder with a rotating auger or linear screw (collectively element 500) in place of the piston. The auger or screw may be moved rotationally by a shaft driven by an electric motor. Compressive force is applied mechanically by the auger or screw to the feedstock 404 within the compression chamber. Moreover, fresh feedstock 502 can be continuously fed into a distal end of the chamber with the assistance of the auger or screw. More particularly, the fresh feedstock 502 is forced into the chamber 403 by the auger or screw mechanically to produce compressed feedstock 404, which is forced through port 406 (extruded) and cut to length by cutter 410 to form pellet 408. The discharge port can be fitted with fixed dies of different diameter to enable application a desired amount of back-pressure to control and shear force at a given feed rate. A ram extruder with a rotating auger or linear screw is another example of a milling apparatus for milling feedstock with moisture content above 8%-15% and even above 20% by weight without reliance on brittle fracture.

The wet milled feed stock can be spread on trays to dry in controlled atmosphere chambers, thereby limiting exposure to adventious contamination and facilitating a reproducible drying schedule. Potential advantages of wet milled feed stock include distribution of cannabinoid oils throughout the cellulose plant material thereby reducing the liability of potency loss due to rough handling of the dried product. Furthermore, the wet milled material can be blended with other solids or liquids prior to drying to effect a defined composition not found in the original plant material.

Regardless of which milling technique or techniques are utilized, the result of the milling process is a flow-able milled feedstock having a predetermined range of particle size and a predetermined average particle size. Depending on particle size and range, the flow-able form may be a type of powder or loose grounds in which individual particles are free to move relative to other particles.

Referring again to FIG. 1, step 104 is to test and blend the flow-able form milled feedstock. Milling the feedstock to a predetermined range of particle size tends to increase feedstock homogeneity and reduce susceptibility to damage associated with processing and handling. The substances of interest are not necessarily evenly distributed in the harvested botanical matter. Cannabinoids, for example, are produced in trichomes which are not uniformly distributed throughout the *cannabis* plant. Milling *cannabis* feedstock produces a flow-able form with more uniformly distributed component substances such as cannabinoids. The increased homogeneity of milled feedstock facilitates testing and blending. Testing may include testing characterizing aspects of a particular feedstock, e.g., potency in terms of concentrations of certain substances. Different milled dried feedstocks may then be combined in order to produce a blended feedstock having desired characteristics such as target concentrations of certain substances. This may be advantageous for therapeutic applications in which the efficacy of a particular feedstock characteristic profile is known and where variability of characteristics is undesirable. A wide variety of mixing devices could be utilized to blend different flow-able feedstocks together to attain a desired characteristic profile.

Step 106 is to form the blended milled feedstock into a state that is suitable for storage, distribution and extraction. While the flow-able feedstock may be efficiently packaged and distributed, compressing the milled feedstock into non-flowable pelletized doses of predetermined size and weight may have certain advantages during extraction as will be explained in greater detail below. The non-flowable form may be a solid mass such as a type of tablet or pellet in which individual particles are not free to move relative to other particles. Any of a wide variety of compression techniques may be utilized to form pellets of compressed, milled feedstock. For example and without limitation, a press or extruder may be used, including but not limited to the examples already described above.

Referring to FIGS. 6A, 6B, 6C and 6D, a continuous process can be achieved with a tablet mill or a flat disk or ring disk pellet mill. In one example a compression chamber is formed by a tube 600 with separate pistons 602, 604 at each of first and second distal ends thereof. As specifically shown in FIG. 6A the first piston 602 is pulled away from the compression chamber so that feedstock 606 can be loaded into the compression chamber. As specifically shown in FIG. 6B the first piston 602 is then used to apply compressive force against the feedstock that was loaded into the compression chamber. A compressed pellet 608 is formed in the chamber when a predetermined amount of pressure has been applied. As specifically shown in FIG. 6C the first piston 602 in then pulled away from the compression chamber 600. As specifically shown in FIG. 6D the second piston 604 is then actuated in order to eject the pellet from the compression chamber. The mill may include multiple compression chambers which operate synchronously.

Regardless of the technique utilized to form compressed pellets of milled feedstock, the pellets may be packaged and labelled for storage and delivery. As will be described below, the compressed pellets may provide some advantages associated with delivery of the therapeutic substances via vaporization. The term "pellet" is used broadly in this disclosure to describe any shape and size of loose material that has been processed into a non-flowable state.

Figure 7:
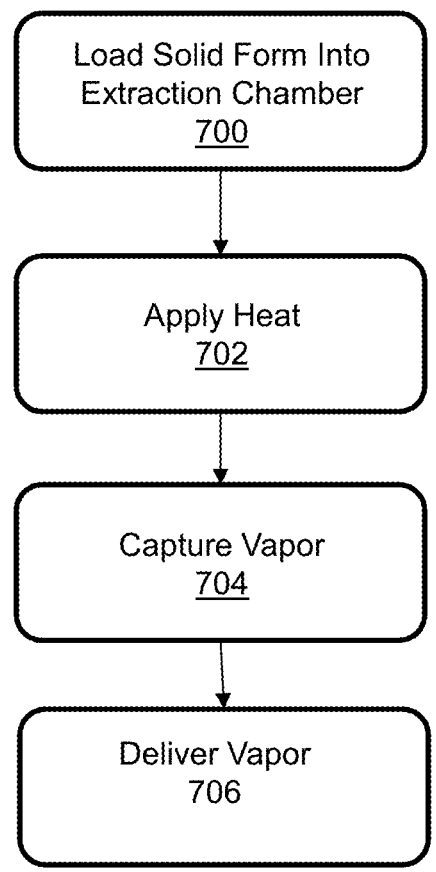
FIG. 7 illustrates a process for vaporizing and delivering the prepared botanical matter.
Figure 8:
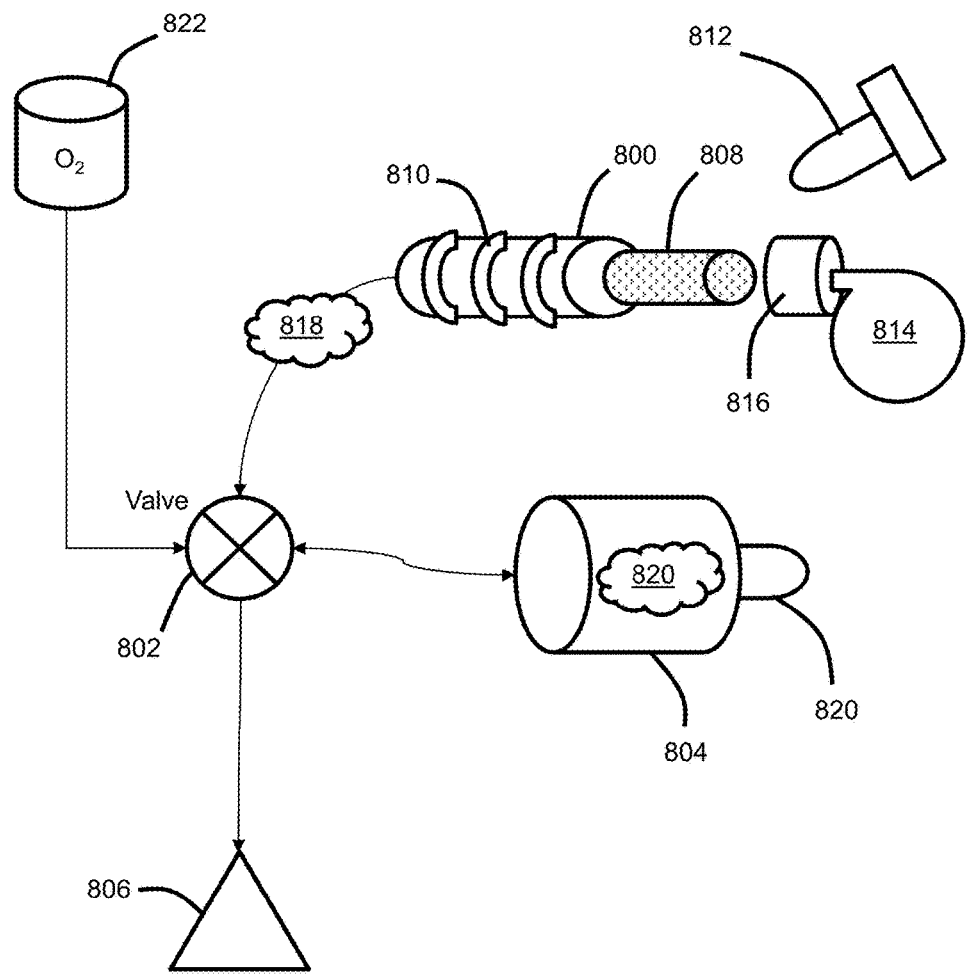
FIG. 8 illustrates a vaporization system.

Referring now to FIGS. 7 and 8, an extraction system may include an extraction chamber 800, a valve 802, a vapor collection chamber 804, and a vapor delivery device 806, interconnected as shown via flexible tubing. A wide variety of fittings could be used for the interconnections, e.g., screw on, snap-fit and press-fit types, without limitation. The valve may be a multi-position, multi-port valve, e.g., 3-port or 4-port type with two or three positions corresponding to different states. The vapor collection chamber may include a syringe barrel and plunger which can be used to adjust the volume of the barrel. The vapor delivery device may include a medical face mask, which may include a filter. A pressure gauge and/or vent may be provided to allow regulation of pressure and temperature.

In an initial step 700 the non-flowable form botanical matter 808, e.g., a pellet formed as described above, is loaded into the extraction chamber 800. The extraction chamber and pellet may have corresponding shapes and dimensions such that the pellet fits snugly within the extraction chamber when loaded therein, e.g., so as to reduce or eliminate free space which might otherwise be occupied by air. However this is not a limitation. For example, the extraction chamber could be loaded from a relatively larger pellet by forcing the open distal end of the extraction chamber against the pellet, thereby shearing off excess portions of the pellet. Moreover, the pellet may fit loosely inside the extraction chamber.

Step 702 is to heat the loaded pellet. The loaded pellet is heated to at least the vaporization temperature of the substances targeted for vaporization. The pellet may contain various substances which are desirable to extract for therapeutic and other purposes. These substances may be found in essential oils and other forms which have a vaporization temperature which is less than the combustion temperature of the pellet. In one implementation the pellet is heated to at least the vaporization temperature of the substances targeted for vaporization but to less than the combustion temperature of the pellet. The heat may be applied conductively, convectively, or both in combination. Conductive heat may be applied, for example, by heating the outer surface of the extraction chamber 800 with a heating element 810 such as an electrically resistive, thermally conductive coil or quartz heater. Other heat sources such as a direct or indirect flame might be utilized. Heat from the heating element 810 is conducted to the extraction chamber 800 and from there to the pellet 808. The diameter of the pellet (and interior of the extraction chamber) may be sized such that the conducted heat is evenly applied to the pellet, e.g., without a significant radial thermal gradient across the pellet. In some implementations conductive heat may be applied by inserting a heated thermal mass element 812 into the open distal end of the extraction chamber, i.e., such that the heated thermal mass element 812 comes into contact with the pellet 808. In some implementations convective heat may be applied by introducing heated gas to the extraction chamber. The heated gas may be provided with a heater/blower component 814. The heater/blower may be connected to a cap 816 which can be attached to the distal end of the chamber 800, e.g., isolating the interior of the chamber from ambient air. However the cap may be used without the heater/blower. The heater/blower provides heated gas which heats the pellet to a temperature which vaporizes the substances of interest without causing combustion. The heated gas may be devoid of oxygen if an anaerobic extraction is desired. However, heated air could be utilized. It should be appreciated that gas (including possibly air) does not necessarily flow through the pellet during vaporization. For example, the pellet and/or the hot gas source may seal the distal end of the extraction chamber. Hot gas introduced via the distal end may displace some of the extracted vapor 818 without flowing into the valve 802 in significant volume. Sealing the distal end of the extraction chamber, e.g., with cap 816, prior to vaporization helps to provide anaerobic extraction. Pelletizing the milled feedstock and avoidance or mitigation of air pockets within the extraction chamber further reduces the presence of oxygen. The pellet may be heated in a wide variety of different ways and the illustrated techniques are merely examples, and not limitations.

In some implementations the pellet may intentionally be heated to a temperature which causes combustion. For example, the heating element or heated gas may heat the pellet to greater than the combustion temperature of the pellet. A direct flame applied to the exterior of the extraction chamber may also heat the pellet to combustion temperatures, and the thermal mass element may be heated to temperatures which cause formation of resins and/or combustion.

The rate of heating of the pellet may also be controlled. For example, the pellet may be rapidly heated or slowly heated. Rapid heating may promote uniform heat flux into the pellet and mitigation of degradation. Moreover, the process cycle time may be shorter if the pellet is heated rapidly. For heat sensitive loads, e.g. those that auto-catalyze their own degradation, applying a vacuum may help to reduce the boiling point of the vaporizable substance, e.g. pulling a partial vacuum with the collection chamber syringe or via inhaling.

Regardless of how heat is applied to the pellet, the application of heat in step 702 causes the substances of interest to vaporize. There are 483 identifiable chemical constituents known to exist in the *cannabis* plant, and at least 85 cannabinoids have been isolated from the plant. While the aromatic terpenoids begin to vaporize at 126.0° C. (258.8° F.), the more bio-active tetrahydrocannabinol (THC), cannabidiol (CBD) and cannabinol (CBN) do not vaporize until near their respective boiling points at atmospheric pressure: THC 157° C. (315° F.), CBD 160-180° C. (320° F.-356° F.), and CBN 185° C. (365° F.).

In step 704 the extracted vapor 818 is captured in the vapor collection chamber 804. This may be accomplished by applying a vacuum to the collection chamber with a pressure adjustment component 820. The vacuum reduces the overall pressure within the extraction chamber, thereby lowering the boiling point of the substances targeted for vaporization. The vapor is drawn into the vapor collection chamber through the tubing which interconnects the extraction chamber with the collection chamber via valve 802. The valve includes ports which are connected to the extraction chamber 800, vapor collection chamber 804 and vapor delivery device 806, respectively, via tubing. In a first position the valve 802 provides a pathway between the extraction chamber and the vapor collection chamber. In a second position the valve provides a pathway between the vapor collection chamber and the vapor delivery device. With the valve in the first position the vapor is drawn from the extraction chamber into the vapor collection chamber by actuating the pressure adjustment component. The flow may assist vaporization, e.g., by drawing heated gas into the pellet 808. In one implementation the vapor collection chamber and pressure adjustment component are provided by a syringe. In other words, the barrel of the syringe serves as the vapor collection chamber and the plunger serves as the pressure adjustment component. A large volume disposable syringe such as those used for parenteral nutrition may be suitable for short term storage and administration. A chilled collection bottle may be suitable for long term storage or subsequent processing of condensed vapor. For longer heat cycles, e.g. vaporization of a large load, the collection chamber may require additional components to thermally isolate it from accumulated heat of the vaporization chamber. The collection chamber may be sized suitably to accommodate the volume of vapor released from the pellet when hot and configured so that atmospheric oxygen is excluded from the vaporization chamber during the heat cycle.

Step 706 is to deliver the captured vapor 820 to a destination, e.g., to a patient undergoing treatment. The valve state is changed from the first position to the second position in order to deliver the captured vapor. The captured vapor is then expelled from the vapor collection chamber 804 by actuating the pressure adjustment component 820, e.g., increasing pressure within the collection chamber. The captured vapor then flows out of the collection chamber to the vapor delivery device 806 via the valve. The vapor delivery device may be a medical face mask. In some implementations the valve may be a 4-port type, e.g., with the fourth port connected to an $O_2$ supply 822 being supplied to the patient. In a first position the valve provides a pathway from the $O_2$ supply to the vapor delivery device 806 and a separate pathway from the extraction chamber to the vapor collection chamber. Hence the patient can be supplied oxygen while vapor is being extracted and collected. In a second position the extraction chamber is isolated while the vapor collection chamber and vapor delivery device are interconnected, possibly with the $O_2$ supply. In this implementation it may not be necessary to utilize the pressure adjustment component to expel captured vapor from the collection chamber because the vapor will be pulled from the chamber by a Venturi effect created by the flow of $O_2$ from the supply to the delivery system across the open port to the vapor collection chamber. For example, the captured vapor may be mixed with $O_2$ provided to a patient being treated.

A number of implementations have been described. Nevertheless, it will be understood that additional modifications may be made without departing from the scope of the inventive concepts described herein, and, accordingly, other implementations are within the scope of the following claims.

What is claimed is:

1. A system comprising:
    a sample of botanical matter which has been rendered into particles of a predetermined range of sizes and compressed into a non-flowable form;
    an extraction chamber into which the sample is loaded;
    a heat source which applies heat to the loaded sample, the heat causing at least one substance within the sample to vaporize;
    a vapor collection chamber;
    a pressure adjustment component that changes pressure in the vapor collection chamber; and
    a conduit via which vapor resulting from vaporization of the at least one substance is captured from the extraction chamber and delivered to the vapor collection chamber.

2. The system of claim 1 wherein the pressure adjustment component changes pressure in the extraction chamber.

3. The system of claim 1 in which the pressure adjustment component and the vapor collection chamber comprise a syringe.

4. The system of claim 1 further comprising a delivery device which facilitates inhalation of the vapor.

5. The system of claim 4 in which the delivery device which facilitates inhalation of the vapor comprises a facemask.

6. The system of claim 1 further comprising a vapor delivery device and a valve, where the valve interconnects the extraction chamber with the vapor collection chamber in a first state, and where the valve interconnects the vapor collection chamber with the vapor delivery device in a second state.

7. The system of claim 1 further comprising a cap which seals the extraction chamber.

8. The system of claim 1 wherein the sample occupies substantially all of the extraction chamber.

9. The system of claim 1 wherein the heat source comprises a conductive heat source.

10. The system of claim 1 wherein the heat source comprises a convective heat source.

11. The system of claim 1 wherein the sample is heated by the heat source to at least a boiling point of the at least one substance but not to a decomposition temperature of the sample.

12. The system of claim 1 wherein the sample is heated by the heat source to at least a combustion temperature of the sample.

13. The system of claim 1 wherein the extraction chamber comprises a blunt end needle.

14. The system of claim 1 comprising a rendering device that renders the sample into particles of the predetermined range of sizes in a wet milling process in which feedstock has a moisture content of at least 20% by weight.

15. The system of claim 14 wherein the rendering device comprises a ram extruder.

* * * * *